United States Patent [19]

Yamashita et al.

[11] Patent Number: 5,101,054

[45] Date of Patent: Mar. 31, 1992

[54] NOVEL FLUORINE-CONTAINING PLATINUM COMPLEX

[75] Inventors: Tsuneo Yamashita, Settsu; Hiroyuki Iwai, Higashi-Osaka; Kazuhiro Shimokawa, Settsu, all of Japan

[73] Assignee: Daikin Industries, Ltd., Osaka, Japan

[21] Appl. No.: 613,888

[22] PCT Filed: Apr. 4, 1990

[86] PCT No.: PCT/JP90/00454

§ 371 Date: Dec. 4, 1990

§ 102(e) Date: Dec. 4, 1990

[87] PCT Pub. No.: WO90/12018

PCT Pub. Date: Oct. 18, 1990

[30] Foreign Application Priority Data

Apr. 4, 1989 [JP] Japan ................... 1-86095

[51] Int. Cl.$^5$ ............................. C07F 15/00
[52] U.S. Cl. ............................. 556/137; 556/40
[58] Field of Search ............ 556/137, 136, 40; 514/492

[56] References Cited

U.S. PATENT DOCUMENTS

| | | | |
|---|---|---|---|
| 4,921,984 | 5/1990 | Nowatari et al. | 556/137 X |
| 4,937,358 | 6/1990 | Bitha et al. | 556/137 X |
| 5,028,727 | 7/1991 | Verbeek et al. | 556/137 |
| 5,034,553 | 7/1991 | Verbeek et al. | 556/137 |

Primary Examiner—Arthur C. Prescott
Attorney, Agent, or Firm—Birch, Stewart, Kolasch & Birch

[57] ABSTRACT

A fluorine-containing platinum complex having anti-tumor activity of the formula:

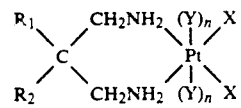

wherein
$R_1$ is a fluorine atom or a trifluoromethyl group,
$R_2$ is a fluorine atom, a hydrogen atom or a lower alkyl group,
X is a halogen atom, a group of the formula: $-NO_2$, or two Xs combined to form a group of the formulae:

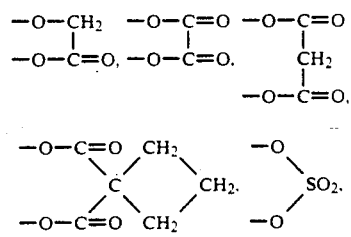

Y is a hydroxyl group or a halogen atom, and
n is 0 or 1, and an anti-tumor composition comprising the same as an active ingredient.

13 Claims, No Drawings

NOVEL FLUORINE-CONTAINING PLATINUM COMPLEX

TECHNICAL FIELD

The present invention relates to a novel fluorine-containing platinum complex and a pharmaceutical composition containing the same. The fluorine-containing platinum complex of the present invention has growth inhibitory activity of towards cancer cells, and is expected to be useful as an anti-tumor agent.

PRIOR ART

It is known that cisplatin [chemical name: cis-dichlorodiamine platinum (II), hereinafter referred to as CDDP] has potent anti-tumor activity, particularly against various kinds of solid cancers. However, CDDP has some side effects such as toxicity to the kidneys, and vomiting. Especially when it is employed clinically, the dose thereof must be limited owing to the toxicity to the kidneys. Hence, the anti-tumor effect thereof cannot be fully obtained. Further, there have been many problems, such as that CDDP does not exhibit sufficient anti-tumor activity against tumor cells which have already become cisplatin resistant (drug resistance), and the like.

Although there have been many attempts to prepare various new derivatives, none has succeeded in satisfying the need for strong anti-tumor activity, effectiveness against tumor cells having drug-resistance, and low toxicity.

There have been prepared many platinum complexes as derivatives having the above-mentioned anti-tumor activity, and some of them have been reported to have anti-tumor activity. The present inventors have intensively studied to obtain a platinum complex having more improved anti-tumor activity, have prepared various platinum complexes wherein a specific fluorine-containing 1,3-propanediamine is used as a ligand, and have found that those complexes have stronger anti-tumor activity than conventional derivatives, and are effective against tumor cells which have already become drug resistant, and further have fewer side effects. The present invention has been accomplished based on the above findings.

An object of the present invention is to provide a novel fluorine-containing platinum complex which has excellent anti-tumor activity. Another object of the present invention is to provide an anti-tumor composition comprising as an active ingredient the said fluorine-containing platinum complex.

DISCLOSURE OF THE INVENTION

The fluorine-containing platinum complex of the present invention is a compound of the formula:

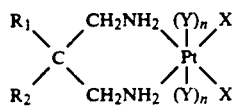

wherein
$R_1$ is a fluorine atom or a trifluoromethyl group,
$R_2$ is a fluorine atom, a hydrogen atom or a lower alkyl group,
X is a halogen atom, a group of the formula: $-ONO_2$, or two Xs combined to form a group of the formulae:

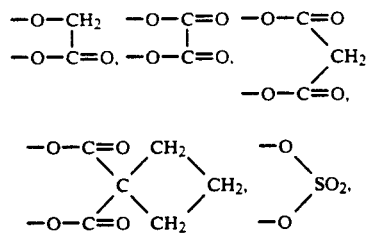

Y is a hydroxyl group or a halogen atom, and
n is 0 or 1.

In the compounds of the above formula (1), the lower alkyl group for $R_2$ is a straight-chain or branched-chain alkyl group having 1 to 4 carbon atoms, such as a methyl group, an ethyl group, an n-propyl group, an isopropyl group, an n-butyl group, a sec-butyl group, a tert-butyl group, and the like. The halogen atom is a fluorine atom, a chlorine atom, a bromine atom or an iodine atom.

Representatives of the compound of the above formula (1) are as follows:
1. Cis-dichloro-(2-methyl-2-trifluoromethyl-1,3-propanediamine) platinum (II)
2. Cis-dichloro-(2-ethyl-2-trifluoromethyl-1,3-propanediamine) platinum (II)
3. Cis-dichloro-(2-trifluoromethyl-1,3-propanediamine) platinum (II)
4. Cis-dinitrato-(2-methyl-2-trifluoromethyl-1,3-propanediamine) platinum (II)
5. Cis-(2-methyl-2-trifluoromethyl-1,3-propanediamine)glycolato platinum (II)
6. Cis-(2-methyl-2-trifluoromethyl-1,3-propanediamine)oxalato platinum (II)
7. Cis-(2-methyl-2-trifluoromethyl-1,3-propanediamine)malonato platinum (II)
8. Cis-(2-methyl-2-trifluoromethyl-1,3-propanediamine)-1,1-cyclobutanedicarboxylato platinum (II)
9. Cis-tetrachloro-(2-methyl-2-trifluoromethyl-1,3-propanediamine) platinum (IV)
10. Cis-dichloro-trans-dihydroxy-(2-methyl-2-trifluoromethyl-1,3-propanediamine) platinum (IV)
11. Cis-2-methyl-2-trifluoromethyl-1,3-propanediamine)sulfato platinum (II)
12. Cis-dichloro-(2-fluoro-1,3-propanediamine) platinum (II)
13. Cis-dichloro-(2-fluoro-2-methyl-1,3-propanediamine) platinum (II)
14. Cis-dichloro-(2,2-difluoro-1,3-propanediamine) platinum (II)
15. Cis-(2-fluoro-1,3-propanediamine)-1,1-cyclobutanedicarboxylato platinum (II)
16. Cis-(2-fluoro-2-methyl-1,3-propanediamine)-1,1-cyclobutanedicarboxylato platinum (II)

The novel fluorine-containing platinum complex of the present invention can be prepared by various methods.

For instance, the fluorine-containing platinum complex of the present invention is prepared by reacting a ligand of the formula:

$$NH_2CH_2-\underset{R_2}{\overset{R_1}{\underset{|}{\overset{|}{C}}}}-CH_2NH_2 \quad (2)$$

wherein $R_1$ and $R_2$ are the same as defined above, with a platinum compound.

The said ligand (2) is prepared by using a fluoroalkyl-malonate as a starting compound by the following processes.

$$\underset{(3)}{\overset{R_1}{\underset{R_2}{>}}C\overset{COOR}{\underset{COOR}{<}}} \xrightarrow{NH_3} \underset{(4)}{\overset{R_1}{\underset{R_2}{>}}C\overset{CONH_2}{\underset{CONH_2}{<}}} \xrightarrow[2)\ HCl]{1)\ B_2H_6}$$

$$\underset{(5)}{\overset{R_1}{\underset{R_2}{>}}C\overset{CH_2NH_2 \cdot HCl}{\underset{CH_2NH_2 \cdot HCl}{<}}} \xrightarrow{K_2CO_3} \underset{(2)}{\overset{R_1}{\underset{R_2}{>}}C\overset{CH_2NH_2}{\underset{CH_2NH_2}{<}}}$$

wherein $R_1$ and $R_2$ are the same as defined above, R is a lower alkyl group such as a methyl group, an ethyl group, and the like.

That is, the desired ligand, the fluorine-containing 1,3-propanediamine (2), is prepared by treating a fluoroalkylmalonate (3) with ammonia in a conventional method to give an acid amide (4), reducing the acid amide (4) with a conventional reducing agent for reducing an acid amide into an amine such as diborane ($B_2H_6$), followed by acidifying with a mineral acid (e.g. hydrochloric acid, etc.) to give a fluorine-containing 1,3-propanediamine mineral acid salt (5) (e.g. hydrochloride, etc.), and further followed by neutralizing with a base such as sodium carbonate, potassium carbonate, sodium hydroxide, potassium hydroxide, and the like.

Besides, the starting compound, fluoroalkylmalonate (3) is prepared by the method disclosed in Japanese Patent Second Publication (Kokoku) No. 62-13941.

Moreover, using the above-mentioned ligand (2), the fluorine-containing platinum complex of the present invention is prepared by the following methods a-e.

Method a

The above compounds 1-3, and 12-14 are prepared by the following method.

$$M_2Pt(Hal)_4 + \underset{(6)}{\overset{R_1}{\underset{R_2}{>}}C\overset{CH_2NH_2}{\underset{CH_2NH_2}{<}}} \underset{(2)}{\longrightarrow}$$

$$\underset{(1a)}{\overset{R_1}{\underset{R_2}{>}}C\overset{CH_2NH_2}{\underset{CH_2NH_2}{<}}\overset{Hal}{\underset{Hal}{>}}Pt} + 2M(Hal)$$

wherein
  M is an atom which can be a monovalent cation, such as potassium, sodium, and the like,
  Hal is a halogen atom, and
  $R_1$ and $R_2$ are the same as defined above.

That is, the platinum complex of the formula (1a), which is a compound of the formula (1) wherein X is a halogen atom, is obtained by reacting a primary platinate halide (6), preferably potassium primary platinate halide with fluorine-containing 1,3-propanediamine (2), which is a ligand, in an aqueous solution such as water or aqueous alcohol at room temperature or at an elevated temperature.

Method b

The above compounds 4-8, 15 and 16 are prepared by the following method.

$$\underset{(1a)}{\overset{R_1}{\underset{R_2}{>}}C\overset{CH_2NH_2}{\underset{CH_2NH_2}{<}}\overset{Hal}{\underset{Hal}{>}}Pt} + 2AgNO_3 \longrightarrow$$

$$\underset{(1b)}{\overset{R_1}{\underset{R_2}{>}}C\overset{CH_2NH_2}{\underset{CH_2NH_2}{<}}\overset{ONO_2}{\underset{ONO_2}{>}}Pt} + 2Ag(Hal)$$

wherein $R_1$ and $R_2$ are the same as defined above.

The dinitrato compound (1b) is obtained by reacting the platinum complex (1a) obtained in above method a with silver nitrate in an aqueous solution at a temperature from room temperature to about 60° C.

The above dinitrato compound (1b) can be converted into the other compounds of the present invention by the following methods (method $b_1$ and method $b_2$).

Method $b_1$ $$(1b) + \overset{HO}{\underset{HO}{>}}R_3 \longrightarrow \underset{(1b-1)}{\overset{R_1}{\underset{R_2}{>}}C\overset{CH_2NH_2}{\underset{CH_2NH_2}{<}}\overset{O}{\underset{O}{>}}Pt\overset{}{\underset{}{>}}R_3}$$

(7)

wherein $R_3$ is a group of the formulae:

$$-\underset{\|}{\overset{O}{C}}-\underset{\|}{\overset{O}{C}}-,\ -\underset{\|}{\overset{O}{C}}-CH_2-\underset{\|}{\overset{O}{C}}-,\ -\underset{\|}{\overset{O}{C}}\underset{CH_2}{\overset{CH_2}{\diagdown}}\underset{CH_2}{\overset{}{\diagup}}C\underset{\|}{\overset{O}{-C-}},$$

$R_1$ and $R_2$ are the same as defined above.

That is, the dicarboxylato compound (1b-1) is obtained by reacting the dinitrato compound (1b) with a dicarboxylic acid, preferably with an alkali metal salt thereof (e.g. potassium salt, etc.) in an aqueous solution at room temperature.

Method $b_2$ $$(1b) \xrightarrow{\text{anion exchange resin}}$$

$$\underset{(8)}{\overset{R_1}{\underset{R_2}{>}}C\overset{CH_2NH_2}{\underset{CH_2NH_2}{<}}\overset{OH}{\underset{OH}{>}}Pt} \xrightarrow{HO-R_4-OH\ (9)}$$

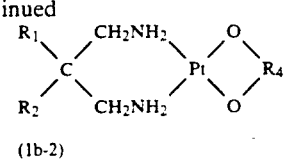
(1b-2)

wherein R₄ is a group of the formulae:

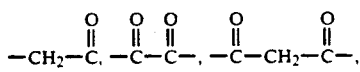

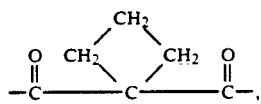

R₁ and R₂ are the same as defined above.

That is, the mono- or dicarboxylato compound (1b-2) is obtained by treating the dinitrato compound (1b) with an anion exchange resin to give the dihydroxy compound (8), followed by reacting the compound (8) with a carboxylic acid (9) in an aqueous solution at room temperature.

Method c

The above compound 9 is prepared by the following method.

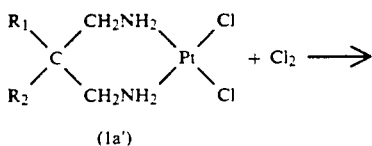
(1a')

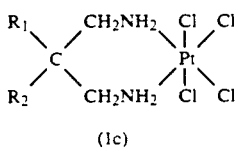
(1c)

wherein R₁ and R₂ are the same as defined above.

The tetrachloro compound (1c) is obtained by dissolving the compound (1a'), which a compound (1a) of the present invention wherein Hal is Cl, in water, followed by blowing chlorine gas with heating into the aqueous solution thereof.

Method d

The above compound 10 is prepared by the following method.

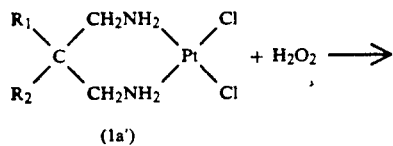
(1a')

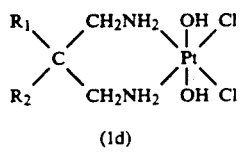
(1d)

The compound (1d) is obtained by adding aqueous hydrogen peroxide solution with heating to an aqueous solution of the compound (1a') as used in the method c.

Method e

The above compound 11 is prepared by the following method.

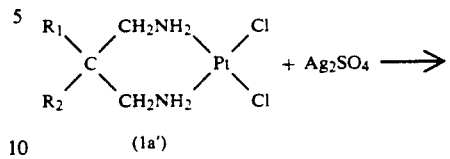
(1a')

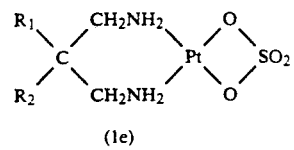
(1e)

The compound (1e) is obtained by reacting the compound (1a') with heating with silver sulfate in an aqueous solution.

The reactions in the above methods a–e are mostly carried out at room temperature, or if necessary, with heating in a water bath. Further, if necessary, these reactions are carried out under shading. The isolation and purification of the desired compound are carried out by separating the crystal which precipitates during the reactions, by filtration, followed by recrystallization from methanol or water, or by concentrating the reaction mixture under reduced pressure, followed by cooling with ice, and then followed by treating the precipitated crystal in the same manner as above.

The mono- or dicarboxylic acid or an alkali metal salt thereof used in the methods b₁ and b₂ are, for example, glycolic acid, oxalic acid, malonic acid, 1,1-cyclobutanedicarboxylic acid, or a sodium salt or potassium salt thereof.

The fluorine-containing platinum complex (1) of the present invention has excellent growth inhibitory activity toward cancer cells, and is expected to be used as an anti-tumor agent in the treatment of various tumors in human or other animals, such as prostatic cancer, orchioncus, ovarian cancer, malignant lymphoma, leukemia, breast cancer, and the like.

The compound of the present invention can be administered by the oral or parenteral route to human or animals, preferably by the parenteral route. When the compound of the present invention is administered parenterally, it may be administered in the form of a solution or a suspension in a suitable solvent (e.g. distilled water for injection, saline solution, 5% aqueous glucose solution, aqueous ethanol, aqueous glycerin solution, aqueous propyreneglycol solution, etc.) by intravenous injection, intramuscular injection, subcutaneous injection, or drip infusion, and the like. In this case, the compound of the present invention may be sealed into an ampoule in the form of a solution or suspension, but preferably preserved in an ampoule or a vial in the form of a crystal, a powder, a microcrystal, or a lyophilized product, and dissolved in a suitable solvent when used. The pharmaceutical preparation of the compound of the present invention may contain a conventional stabilizing agent.

The dose of the platinum complex of the present invention may vary depending on the administration routes, ages and weights of the patients, and the severity of the diseases to be treated, and the like, but it may usually be in the range of about 10–200 mg/kg/day.

BEST MODE FOR CARRYING OUT THE INVENTION

Hereinafter, the process for preparing the compound of the present invention and the pharmaceutical, activity thereof are illustrated by the following Examples and Experiments, but the present invention should not be construed to be limited thereto.

EXAMPLE 1

Preparation of cis-dichloro-(2-methyl-2-trifluoromethyl-1,3-propanediamine) platinum (II)

1-1. Preparation of a ligand:

(1) A solution of dimethyl methyl-trifluoromethylmalonate (7.31 g, 34.15 mmol) in methanol (20 ml) is put into a 100 ml three neck flask equipped with a dry ice-acetone trap and an ammonia installation tube, and cooled to $-10°$ C. Ammonia gas is gradually blown thereto with stirring until ammonia gas starts to reflux, and the mixture is reacted for 5 hours while ammonia gas is continuously added so as to reflux throughout the reaction. The disappearance of the starting ester is monitored by gas chromatography, and the ammonia and methanol are distilled off under reduced pressure. The resulting residue is purified by recrystallization from methanol to give methyl-trifluoromethylmalonamide.

Yield (rate): 7.02 g (89.4%).

Sublimation temperature: 198°–202° C.,

IR spectra (KBr, cm$^{-1}$): 3400, 3350, 3250, 3200, 1700, 1660, 1610, 1460, 1410, 1370, 1280, 1200, 1180, 1120, 670, 635, 580.

(2) A solution of diborane in THF (56.2 ml, 1.78 mmol/ml, 150 mmol) is put into a 100 ml three neck flask equipped with a Dimroth condenser, and cooled in an ice bath. Subsequently, thereto is added gradually with stirring methyl-trifluoromethylmalonamide (8.0 g, 43.5 mmol) prepared in the above (1) in the form of a crystal, and the mixture is reacted at room temperature for 3 hours. After refluxing for 5 hours, the mixture is acidified with 1N aqueous hydrochloric acid solution with cooling, and THF is distilled off under reduced pressure. The reaction mixture is heated at 70° C. for 30 minutes, and thereto is added KOH with cooling until it saturates. The mixture is extracted with diethyl ether twice, and diamine and water are removed from the residue by azeotropic distillation under reduced pressure. The ether layer and aqueous layer are combined, acidified with 5N aqueous hydrochloric acid solution, and the aqueous layer is distilled off under reduced pressure to give 2-methyl-2-trifluoromethyl-1,3-propanediamine hydrochloride.

Yield (rate): 5.72 g (57.4%).

IR spectra (KBr, cm$^{-1}$): 3400, 3200, 3000, 1970, 1700, 1660, 1620, 1600, 1520, 1470, 1280, 1140, 1100, 1080, 1050, 1030, 1000, 840, 730, 700.

1-2. Preparation of the desired platinum complex:

2-Methyl-2-trifluoromethyl-1,3-propanediamine hydrochloride (810 mg) is dissolved in water (5 ml), and thereto is added K$_2$CO$_3$ in order to adjust the pH value of the solution to pH 9–10. Thereto is added K$_2$PtCl$_4$ (840 mg), and the mixture is reacted at room temperature under shading for one day. The precipitated light orange crystal is separated by filtration, washed with a small amount of water, and air-dried to give the desired product, cis-dichloro-(2-methyl-2-trifluoromethyl-1,3-propanediamine) platinum (II) (520 mg, yield; 61.6%).

Melting point: 245° C.–255° C. (decomposed with coloring)

Elemental analysis for C$_5$H$_{11}$N$_2$FCl$_2$Pt: Calcd. (%): C,14.22; H,2.60; N,6.64; F,13.51; Cl,16.82; Found (%): C,14.33; H,2.31; N,6.70; F,13.40; Cl17.10.

IR spectra (KBr, cm$^{-1}$): 3500, 3225, 3130, 1590, 1495, 1465, 1310, 1260, 1205, 1170, 1140, 1110, 1030, 960, 810, 715, 655.

$^{19}$F-NMR spectra (DMSO-d$_6$, TFA standard, regarding high magnetic field as +): δ 2.9 (s).

$^1$H-NMR spectra (DMSO-d$_6$, TMS standard): δ 1.28 (s, 3H, CH$_3$—), 2.65–3.08 (m, 4H, —CH$_2$—).

EXAMPLE 2

Preparation of cis-(2-methyl-2-trifluoromethyl-1,3-propanediamine)-1,1-cyclobutanedicarboxylato platinum (II)

The compound obtained in Example 1 (300 mg) is reacted with heating with pure water (10.0 ml) containing silver nitrate (241 mg) at 60° C. under shading for 3 hours. The silver chloride is filtered off, and to the filtrate is added 5% aqueous KCl solution so as to remove unreacted silver nitrate. The filtrate is concentrated to give cis-dinitrato-(2-methyl-2-trifluoromethyl-1,3-propanediamine) platinum (II) (171 mg, 51.0%). The resulting dinitrato compound is dissolved in pure water (2.0 ml), and thereto is added potassimm 1,1-cyclobutanedicarboxylate (156 mg). The mixture is allowed to stand at room temperature under shading for one day. The mixture is concentrated under reduced pressure, and crystallized in a cool place. The precipitated crystal is separated by filtration, washed with water, and air-dried to give cis-(2-methyl-2-trifluoromethyl-1,3-propanediamine)-1,1-cyclobutanedicarboxylato platinum (II) (90 mg, 25.7%).

Melting point: 215° C. (decomposed with coloring).

IR spectra (KBr, cm$^{-1}$): 3430, 3200, 3100, 2900, 1640, 1360, 1330, 1250, 1230, 1200, 1110, 1025, 900, 845.

EXAMPLE 3

Preparation of cis-dichloro-(2-fluoro-1,3-propanediamine) platinum (II)

2-Fluoro-1,3-propanediamine hydrochloride (200 mg, 1.22 mmol) obtained in the same manner as in Example 1-1 is dissolved in water (2.0 ml), and the pH value thereof is adjusted to 8.5. Thereto is added with stirring potassium platinate chloride (253 mg, 0.61 mmol), and the mixture is reacted at room temperature under shading for one day. The precipitated crystal is collected by filtration, washed with a small amount of water, and air-dried to give the desired product, cis-dichloro-(2-fluoro-1,3-propanediamine) platinum (II).

Yield (rate): 150 mg (68.9%).

Melting point: 265° C. (decomposed with coloring).

IR spectra (KBr, cm$-1$): 3250, 3200, 3120, 1590, 1195, 1180, 1025, 945, 840.

$^1$H-NMR spectra (DMSO-d$_6$, TMS standard): δ 2.65–3.26 (m, 4H, CH$_2$—), 5.20 (d, J$_{F-H}$=42.9 Hz, 1H, F—CH—).

$^{19}$F-NMR spectra (DMSO-d$_6$, TFA standard, regarding the high magnetic field as +): δ 114.5 (dt, J$_{F-H}$=42.9 Hz).

Elemental analysis for C$_3$H$_9$N$_2$FCl$_2$Pt: Calcd. (%): C,10.6; H,2.51; N,7.82; F,5.31; Cl19.83; Found (%): C,9.99; H,2.32; N,7.76; F,5.50; Cl20.5.

EXAMPLE 4

Preparation of cis-dichloro-(2-fluoro-2-methyl-1,3-propanediamine) platinum (II)

2-Fluoro-2-methyl-1,3-propanediamine hydrochloride (400 mg. 2.25 mmol) obtained in the same manner as in Example 1-1 and potassium platinate chloride (470 mg. 1.13 mmol) are treated in the same manner as in Example 1 in pure water (4.0 ml) to give the desired cis-dichloro-(2-fluoro-2-methyl-1,3-propanediamine) platinum (II).

Yield (rate): 603 mg (72.0%).

Melting point: 257° C. (decomposed with coloring).

IR spectra (KBr, cm$^{-1}$): 3300, 3200, 3130, 1590, 1585, 1235, 1180, 1160, 1150, 1030, 865, 820.

$^1$H-NMR spectra (DMSO-d$_6$, TMS standard): δ 1.14 (d, $J_{F-H}$=22.9 Hz, 3H, CH$_3$—C), 2.65–3.20 (m, 4H, CH$_2$—).

$^{19}$H-NMR spectra (DMSO-d$_6$, TFA standard, regarding the high magnetic field as +): δ 80.8 (m, 1F).

Elemental analysis for C$_4$H$_{11}$N$_2$FCl$_2$Pt: Calcd. (%): C,12.90; H,2.96; N,7.53; F,5.11; Cl19.09; Found (%): C,12.90; H,2.76; N,7.40; F,4.50; Cl17.70.

EXAMPLE 5

Preparation of cis-dichloro-(2,2-difluoro-1,3-propanediamine) platinum (II)

2,2-Difluoro-1,3-propanediamine hydrochloride (570 mg. 3.11 mmol) obtained in the same manner as in Example 1-1 and potassium platinate chloride (944 mg, 2.25 mmol) are treated in pure water (5.0 ml) in the same manner as in Example 1 to give desired cis-dichloro-(2,2-difluoro-1,3-propanediamine) platinum (II).

Yield (rate): 580 mg (68.6%).

Melting point: 190° C. (decomposed with coloring).

IR spectra (KBr, cm$^{-1}$): 3500, 3250, 3200, 3125, 1600, 1250, 1125, 1070, 1045, 950.

$^1$H-NMR spectra (DMSO-d$_6$, TMS standard): δ 2.80–3.36 (m, 4H, —CH$_2$—).

$^{19}$F-NMR spectra (DMSO-d$_6$, TFA standard, regarding the high magnetic field as +): δ 22.9 (quint, J=14.3 Hz).

EXAMPLE 6

Preparation of cis-(2-fluoro-1,3-propanediamine)-1,1-cyclobutanecarboxylato platinum (II)

The compound obtained in Example 3 (180 mg, 0.50 mmol) is suspended in pure water, and thereto is added silver nitrate (170 mg, 1.00 mmol), and reacted at 60° C. under shading for 3 hours. The precipitated silver chloride is removed by filtration, and to the filtrate is added 0.5% aqueous KCl solution so as to precipitate unreacted silver nitrate in the form of silver chloride. The precipitated silver chloride is removed by filtration, thereto is added potassium 1,1-cyclobutanecarboxylate (110 mg, 0.50 mmol), and the mixture is reacted at room temperature for 3 days. The reaction mixture is concentrated under reduced pressure and cooled with ice. The precipitated crystal is collected by filtration, and washed with a small amount of cold water and acetone to give desired cis-(2-fluoro-1,3-propanediamine)-1,1-cyclobutanedicarboxylato platinum (II).

Yield (rate): 80 mg (39.9%).

Melting point: 230° C. (decomposed).

IR spectra (KBr, cm$^{-1}$): 3450, 3200, 3100, 2950, 1645, 1365, 1335, 1250, 1200, 1110, 1030, 955, 900, 845, 470.

EXAMPLE 7

Preparation of cis-(2-fluoro-2-methyl-1,3-propanediamine)-1,1-cyclobutane-dicarboxylato platinum (II)

The compound obtained in Example 4 (400 mg, 1.08 mmol) is treated in the same manner as in Example 6 by using silver nitrate (370 mg, 2.16 mmol) and potassium 1,1-cyclobutanedicarboxylate (240 mg, 1.08 mmol) to give desired cis-(2-fluoro-2-methyl-1,3-propanediamine)-1,1-cyclobutanedicarboxylato platinum (II).

Yield (rate): 90 mg (21.8%).

Melting point: 220° C. (decomposed).

IR spectra (KBr, cm$^{-1}$): 3250, 3100, 2975, 1600, 1460, 1385, 1350, 1280, 1255, 1160, 1110, 1090, 1040, 910, 880, 565, 470.

EXAMPLE 8

Preparation of cis-dichloro-(2-ethyl-2-trifluoromethyl-1,3-propanediamine) platinum (II)

2-Ethyl-2-trifluoromethyl-1,3-propanediamine hydrochloride (100 mg, 0.41 mmol) obtained in the same manner as in Example 1-1 is dissolved in water (1.0 ml), and the pH value thereof is adjusted to 8.5. Thereto is added with stirring potassium platinate chloride (87 mg, 0.21 mmol). The mixture is reacted at room temperature under shading for one day. The precipitated crystal is collected by filtration, washed with a small amount of water, and air-dried to give desired cis-dichloro-(2-ethyl)-trifluoromethyl-1,3-propanediamine) platinum (II).

Yield (rate): 53 mg (57.9%).

EXAMPLE 9

Preparation of cis-(2-methyl-2-trifluoromethyl-1,3-propanediamine)-malonato platinum (II)

The dinirato compound obtained in Example 2 (50 mg, 0.11 mmol) is passed through the anion exchange resin (Amberlite IRA-400) to give an aquo compound, and thereto is added malonic acid (12 mg, 0.12 mmol) and stirred under shading for one day to give cis-(2-methyl-2-trifluoromethyl-1,3-propanediamine)-malonato platinum (II).

Yield (rate): 30 mg (60.2%).

EXAMPLE 10

Preparation of cis-(2-methyl-2-trifluoromethyl-1,3-propanediamine)oxalato platinum (II)

The dinitrato compound obtained in Example 2 (50 mg, 0.11 mmol) is passed through the anion exchange resin (Amberlite IRA-400) to give an aquo compound, and thereto is added oxalic acid (10 mg, 0.11 mmol) and stirred under shading for one day to give cis-(2-methyl-2-trifluoromethyl-1,3-propanediamine)oxalato platinum (II).

Yield (rate): 25 mg (51.5%).

EXAMPLE 11

Preparation of
cis-(2-methyl-2-trifluoromethyl-1,3-propanediamine)-glycolato platinum (II)

The dinitrato compound obtained in Example 2 (50 mg, 0.11 mmol) is passed through the anion exchange resin (Amberlite IRA-400) to give an aquo compound, and thereto is added glycolic acid (10 mg, 0.14 mmol) and stirred under shading for one day to give cis-(2-methyl-2-trifluoromethyl-1,3-propanediamine)-glycolato platinum (II).

Yield (rate): 27 mg (58.3%).

EXAMPLE 12

Preparation of
cis-tetrachloro-(2-methyl-2-trifluoromethyl-1,3-propanediamine) platinum (IV)

The compound obtained in Example 1 (120 mg) is suspended in pure water (15 ml). The mixture is heated at 70° C. and thereto is blown $Cl_2$ gas for 10 minutes. After completion of the reaction, thereto is blown air at 70° C. so as to remove the excess $Cl_2$ gas, and the mixture is cooled to room temperature to give cis-tetrachloro-(2-methyl-2-trifluoromethyl-1,3-propanediamine) platinum (IV).

Yield (rate): 89 mg (64.5%).

EXAMPLE 13

Preparation of
cis-dichloro-trans-dihydroxy-(2-methyl-2-trifluoromethyl-1,3-propanediamine) platinum (IV)

The compound obtained in Example 1 (100 mg) is suspended in pure water (15 ml), and thereto is added dropwise with stirring 30% aqueous hydrogen peroxide solution (0.5 ml). The mixture is reacted at 60° C. under shading for 3 hours, and allowed to stand for one day. The mixture is concentrated, and the precipitated crystal is collected by filtration to give cis-dichloro-trans-dihydroxy-(2-methyl-2-trifluoromethyl-1,3-propanediamine) platinum (IV).

Yield (rate): 48 mg (43.8%).

EXAMPLE 14

Preparation of
cis-(2-methyl-2-trifluoromethyl-1,3-propanediamine)-sulfato platinum (II)

The compound obtained in Example 1 (100 mg) is suspended in pure water (15 ml), and thereto is added silver sulfate (90 mg). The mixture is reacted under at 60° C. shading for 3 hours. The silver chloride is removed by filtration, and the filtrate is concentrated to give cis-(2-methyl-2-trifluoromethyl-1,3-propanediamine)sulfato platinum (II).

Yield (rate): 73 mg (69.7%).

Experiment 1 (anti-tumor activity test)

Mouse leukemia cells L1210 ($1 \times 10^5$) were implanted intraperitoneally to $CDF_1$ mice (female, aged: 8 weeks) on the 0 day of implantation. CDDP and CBDCA were used as a reference. The anti-tumor activity of the platinum complexes in L1210 implanted mice were expressed by the T/C value, which was determined according to the following equation, and by the number of mice which survived until the 30th day of implantation.

$$T/C (\%) = \frac{\text{The average survived days of treated animals}}{\text{The average survived days of control animals}} \times 100$$

The results are shown in Table 1.

TABLE 1

| Test Compound | Dose (mg/kg) | T/C (%) | Number of survived mice (on 30th day) |
|---|---|---|---|
| Compound of Ex. 1 | 12.5 | >304 | 3/6 |
|  | 25 | 375 | 6/6 |
|  | 50 | 273 | 0/6 |
| Compound of Ex. 2 | 50 | 192 | 0/6 |
|  | 100 | 267 | 0/6 |
| CDDP | 6.25 | 227 | 0/6 |
|  | 12.5 | 282 | 1/6 |
|  | 25 | 367 | 4/6 |
| CBDCA | 12.5 | 139 | 0/6 |
|  | 25 | 199 | 0/6 |
|  | 50 | 340 | 2/6 |
|  | 100 | 366 | 2/6 |

Note)
CBDCA. cis-diamino-1,1-cyclobutanedicarboxylato platinum (II)

Experiment 2

The growth inhibitory ratio of cisplatin resistant mouse leukemia cells L1210 (L1210/CDDP) was calculated by comparing cell numbers of the drug-treated group with that of a drug-untreated group, and the $IC_{50}$ value (the concentration of drug which inhibits the growth of cells by 50%) was determined; the $IC_{50}$ values to L1210 cells were also determined. The drug sensitivity (a) was determined according to the following equation.

$$\frac{IC_{50} L1210/CDDP}{IC_{50} L1210} = \text{drug sensitivity } (a)$$

The results are shown in Table 2.

TABLE 2

| Test Compound | $IC_{50}$ L1210/CDDP (μg/ml) | $LC_{50}$ L1210 (μg/ml) | a |
|---|---|---|---|
| Compound of Ex. 1 | 0.10 | 0.90 | 1.1 |
| CDDP | 0.50 | 0.08 | 6.3 |
| CBDCA | 1.82 | 0.25 | 7.3 |

Experiment 3

Test compounds were administered to ICR mice (aged: 8 weeks) on the 1st day, the 5th day and the 9th day. The blood was collected therefrom on the 12th day, and the concentrations of blood urea nitrogen (BUN) were determined.

The results are shown in Table 3.

TABLE 3

| Test Compound | Dose (mg/kg) | Difference of** weights (g) | BUN value (mg/dl) |
|---|---|---|---|
| Control* | None | −0.1 | 27.2 ± 1.9 |
| Compound of Ex. 1 | 25 | −2.3 | 23.3 |
|  | 50 | −5.4 | 17.8 |
| CDDP | 18 | −4.8 | 83.7 |
|  | 25 | −8.9 | 112.3 ± 16.6 |
| CBDCA | 100 | −3.0 | 21.0 ± 4.0 |

*Control group: drug-untreated normal mouse
**Difference of weights = the average weight at the 12th day - the average weight at the 1st day.

We claim:
1. A fluorine-containing platinum complex of the formula:

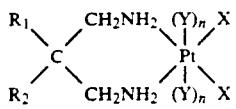

wherein
$R_1$ is a fluorine atom or a trifluoromethyl group,
$R_2$ is a fluorine atom, a hydrogen atom, or a lower alkyl group,
X is a halogen atom, a group of the formula: —NO$_2$, or two Xs combined to form a group of the formulae:

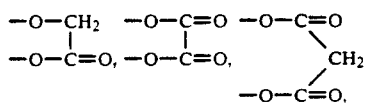

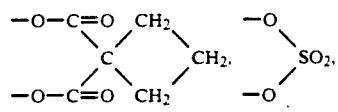

Y is a hydroxyl group or a halogen atom, and n is 0 or 1.

2. The compound according to claim 1, wherein $R_1$ is a trifluoromethyl group, and $R_2$ is a $C_1$–$C_4$ alkyl group or a hydrogen atom.

3. The compound according to claim 2, wherein n is 0.

4. The compound according to claim 3, wherein X is a chlorine atom.

5. The compound according to claim 3, wherein X is a group of the formula: —ONO$_2$ or two Xs combined to form a group of the formulae:

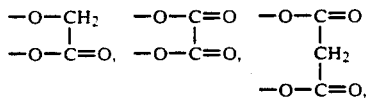

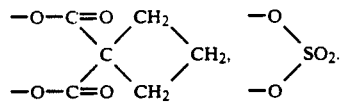

6. The compound according to claim 1, wherein $R_1$ is a fluorine atom, $R_2$ is a fluorine atom, a hydrogen atom or a $C_1$–$C_4$ alkyl group, and n is 0.

7. The compound according to claim 6, wherein X is a chlorine atom.

8. The compound according to claim 6, wherein two Xs combine to form a group of the formula:

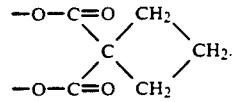

9. The compound according to claim 1, which is selected from the group consisting of:
Cis-dichloro-(2-methyl-2-trifluoromethyl-1,3-propanediamine) platinum (II),
Cis-dichloro-(2-ethyl-2-trifluoromethyl-1,3-propanediamine) platinum (II),
Cis-dichloro-(2-trifluoromethyl-1,3-propanediamine) platinum (II),
Cis-dinitrato-(2-methyl-2-trifluoromethyl-1,3-propanediamine) platinum (II),
Cis-(2-methyl-2-trifluoromethyl-1,3-propanediamine)glycolato platinum (II),
Cis-(2-methyl-2-trifluoromethyl-1,3-propanediamine)oxalate platinum (II),
Cis-(2-methyl-2-trifluoromethyl-1,3-propanediamine)malonato platinum (II),
Cis-(2-methyl-2-trifluoromethyl-1,3-propanediamine)-1,1-cyclobutanedicarboxylato platinum (II),
Cis-tetrahydro-(2-methyl-2-trifluoromethyl-1,3-propanediamine) platinum (IV),
Cis-dichloro-trans-dihydroxy-(2-methyl-2-trifluoromethyl-1,3-propanediamine) platinum (IV),
Cis-(2-methyl-2-trifluoromethyl-1,3-propanediamine)sulfato platinum (II),
Cis-dichloro-(2-fluoro-1,3-propanediamine) platinum (II),
Cis-dichloro-(2-fluoro-2-methyl-1,3-propanediamine) platinum (II),
Cis-dichloro-(2,2-difluoro-1,3-propanediamine) platinum (II),
Cis-(2-fluoro-1,3-propanediamine)-1,1-cyclobutanedicarboxylate platinum (II), and
Cis-(2-fluoro-2-methyl-1,3-propanediamine)-1,1-cyclobutanedicarboxylate platinum (II).

10. An anti-tumor composition, which comprises as an active ingredient an effective amount of the compound according to claim 1, and a pharmaceutically acceptable carrier or diluent.

11. The compound according to claim 2, wherein said $R_2$ $C_1$–$C_4$ alkyl group is a straight-chain or branched-chain group.

12. The compound according to claim 11, wherein said $R_2$ $C_1$–$C_4$ alkyl group is selected from the group consisting of a methyl group, an ethyl group, an n-propyl group, an isopropyl group, an n-butyl group, a sec-butyl group, and a tert-butyl group.

13. The compound according to claim 1, wherein said halogen atom X is selected from the group consisting of a fluorine atom, a chlorine atom, a bromine atom, and an iodine atom.

* * * * *